United States Patent
Toda (10) Patent No.: US 12,127,561 B2
(45) Date of Patent: Oct. 29, 2024

(54) MICROBIAL TREATMENT SOLUTION AND METHOD OF PRODUCING MICROBIAL TREATMENT SOLUTION

(71) Applicant: SUN HOPE CO., LTD., Chiba (JP)

(72) Inventor: Masami Toda, Chiba (JP)

(73) Assignee: SUN HOPE CO., LTD. (JP)

(*) Notice: Subject to any disclaimer, the term of this patent is extended or adjusted under 35 U.S.C. 154(b) by 0 days.

(21) Appl. No.: 18/576,386

(22) PCT Filed: Jun. 10, 2022

(86) PCT No.: PCT/JP2022/023446
§ 371 (c)(1),
(2) Date: Jan. 4, 2024

(87) PCT Pub. No.: WO2023/281981
PCT Pub. Date: Jan. 12, 2023

(65) Prior Publication Data
US 2024/0260580 A1    Aug. 8, 2024

(51) Int. Cl.
D06M 16/00    (2006.01)
A01N 59/08    (2006.01)
A01P 1/00     (2006.01)

(52) U.S. Cl.
CPC ............... *A01N 59/08* (2013.01); *A01P 1/00* (2021.08)

(58) Field of Classification Search
None
See application file for complete search history.

(56) References Cited

U.S. PATENT DOCUMENTS

2008/0008621 A1* 1/2008 Ikeda .................. A61L 2/18
510/161

FOREIGN PATENT DOCUMENTS

| | | | | |
|---|---|---|---|---|
| CN | 110282808 A | * | 9/2019 | ............ A01N 59/00 |
| JP | 10182325 A | | 7/1998 | |
| JP | 11228316 A | | 8/1999 | |
| JP | 2002249407 A | | 9/2002 | |
| JP | 2011153095 A | | 8/2011 | |
| JP | 2014009227 A | | 1/2014 | |
| JP | 2016060949 A | | 4/2016 | |
| JP | 2019155304 A | | 9/2019 | |
| WO | 03055591 A1 | | 7/2003 | |
| WO | 2006057311 A1 | | 6/2006 | |

* cited by examiner

*Primary Examiner* — Susan T Tran (57) ABSTRACT

The microbial treatment solution according to the present invention includes an acidic hypochlorous acid water and a quantum water. The acidic hypochlorous acid water is at a concentration of 0.5 wt % to 5.0 wt % for the total microbial treatment solution, and the quantum water is 90.0 wt % to 99.5 wt % for the total microbial treatment solution. The quantum water is water passed through a quantum water converter, the quantum water converter comprising a container having an inlet and an outlet and plural fragments installed in the container. The fragment is made of austenitic stainless steel or martensitic stainless steel, and the fragment has a regular hexagonal prism shape. The fragment has a hole that penetrates a bottom surface and a top surface of the fragment, the hole is a circular cross section. The fragment has a spiral groove going around an inner surface of the hole at least once, and the fragment is heat-treated. The plural fragments are arranged so that a central axis of the fragments is parallel to each other, and the arrangement is maintained. The arranged plural fragments are positioned between the inlet and the outlet.

10 Claims, 4 Drawing Sheets

FIG. 1

| Test area | | 0 | 1 | 5 | 60 | 1440 | 43200 |
|---|---|---|---|---|---|---|---|
| Example 1 | Viable bacteria count (CFU/100 ml) | 6.3E+07 | <1.0E+2 | <1.0E+2 | <1.0E+2 | <1.0E+2 | <1.0E+2 |
| | Viable bacteria reduction rate (%) | — | >99.99 | >99.99 | >99.99 | >99.99 | >99.99 |
| Reference Example 1 | Viable bacteria count (CFU/100 ml) | 6.3E+07 | 5.6E+07 | 4.1E+07 | 3.0E+07 | 6.3E+07 | 6.3E+07 |
| | Viable bacteria reduction rate (%) | — | — | — | — | — | — |
| Comparative Example 1 | Viable bacteria count (CFU/100 ml) | 6.3E+07 | <1.0E+2 | <1.0E+2 | <1.0E+2 | <1.0E+2 | 8.8E+06 |
| | Viable bacteria reduction rate (%) | — | >99.99 | >99.99 | >99.99 | >99.99 | 86.57 |
| Comparative Example 2 | Viable bacteria count (CFU/100 ml) | 6.3E+07 | 3.6E+07 | 2.1E+07 | 1.9E+07 | 3.6E+07 | 2.5E+07 |
| | Viable bacteria reduction rate (%) | — | 35.71 | 36.59 | 36.67 | 39.29 | 17.71 |

Leaving time (minute)

MICROBIAL TREATMENT SOLUTION AND METHOD OF PRODUCING MICROBIAL TREATMENT SOLUTION

TECHNICAL FIELD

The present invention relates to a microbial treatment solution and a method for producing microbial treatment solution.

BACKGROUND ART

There is conventionally a quantum water that has various effects. For example, WO 03/05591 discloses a liquid treatment apparatus comprising a container having an inlet and an outlet, and plural fragments installed in the container. The fragment is made of austenitic stainless steel or martensitic stainless steel, and the fragment has a regular hexagonal prism shape. The fragment has a hole that penetrates a bottom surface and a top surface of the fragment, the hole is a circular cross section. The fragment has a spiral groove going around an inner surface of the hole at least once, and the fragment is heat-treated. The plural fragments are arranged so that a central axis (the central axis is parallel to six sides of the regular hexagonal prism and perpendicular to both end faces of the regular hexagonal prism) of the fragments are parallel to each other, and the arrangement is maintained. The arranged plural fragments are positioned between the inlet and the outlet. In this way, it is possible to produce the quantum water changed to a state suitable for humans, animals and plants. The quantum water has effects such as hydrogen generation, sterilization, deodorization, lactic acid bacteria growth, surface activity, chlorine detoxification, enzyme activation, and the like.

On the other hand, due to an influence of the new coronavirus infection, a hypochlorous acid water is widely used because it is effective in inactivating viruses and bacteria. For example, JP-A-2016-60949 (PTL2) discloses an electrolytic device comprising an electrolytic cell, a first line, and a second line. The electrolytic cell includes an anode chamber having an anode electrode, an intermediate chamber partitioned from the anode chamber by an anion exchange membrane, inorganic chloride particles accommodated in the intermediate chamber, and a cathode chamber partitioned from the intermediate chamber by a cation exchange membrane and having a cathode electrode. The first line takes out hypochlorous acid water from the anode chamber, and the second line takes out alkaline water from the cathode chamber. In this way, it is possible to provide a compact and low-cost electrolytic apparatus, and help to produce hypochlorous acid water.

Here, the hypochlorous acid water produced in the electrolytic cell or the hypochlorous acid water produced by applying Plasmacluster technology, which is one of the "weak charge technologies", and the both are acidic and safe. And a chlorine concentration for the hypochlorous acid water is high without a use of hydrochloric acid. An acidic hypochlorous acid water includes strongly acidic hypochlorous acid water, weakly acidic hypochlorous acid water, and slightly acidic hypochlorous acid water.

CITATION LIST

Patent Literature

[PTL1] WO 03/055591
[PTL2] JP-A-2016-60949

SUMMARY OF INVENTION

Technical Problem

Here, although there is a constant sterilizing power in the quantum water, there is a problem that the quantum water cannot inactivate the virus of the new coronavirus infection. On the other hand, although the acidic hypochlorous acid water can inactivate the virus of the new coronavirus infection, when the acidic hypochlorous acid water is left for a long period of time, a chlorine concentration (a residual chlorine concentration) for the acidic hypochlorous acid water decreases and there is a problem that the sterilizing power is lost.

Accordingly, the present invention was created as a solution for the problems and aims at providing a microbial treatment solution and a method for producing a microbial treatment solution that can maintain the sterilizing power of acidic hypochlorous acid water for a long period of time.

The microbial treatment solution according to the present invention includes an acidic hypochlorous acid water and a quantum water. The acidic hypochlorous acid water is at a concentration of 0.5 wt % to 5.0 wt % for the total microbial treatment solution, and the quantum water is 90.0 wt % to 99.5 wt % of the total microbial treatment solution. The quantum water is water passed through a quantum water converter, the quantum water converter comprising a container having an inlet and an outlet and plural fragments installed in the container. The fragment is made of austenitic stainless steel or martensitic stainless steel, and the fragment has a regular hexagonal prism shape. The fragment has a hole that penetrates a bottom surface and a top surface of the fragment, the hole is a circular cross section. The fragment has a spiral groove going around an inner surface of the hole at least once, and the fragment is heat-treated. The plural fragments are arranged so that a central axis of the fragments is parallel to each other, and the arrangement is maintained. The arranged plural fragments are positioned between the inlet and the outlet.

The method for producing a microbial treatment solution according to the present invention includes a mixing step. The mixing step mixes an acidic hypochlorous acid water at a concentration of 0.5 wt % to 5.0 wt % for the total microbial treatment solution and a quantum water at a concentration of 90.0 wt % to 99.5 wt % for the total microbial treatment solution.

Advantageous Effects of the Invention

According to the present invention, it is possible to maintain the sterilizing power of the acidic hypochlorous acid water for a long period of time.

DESCRIPTION OF EMBODIMENTS

Hereinafter, an embodiment of according to the present invention will be described with reference to the accompanying drawings, the understanding of the present invention. It should be noted that the following embodiment is an example in which the present invention is embodied, and does not limit the technical scope of the present invention.

The present inventor has been dealing with an acidic hypochlorous acid water and a quantum water for many years, and has been pondering a problem of the fact that the sterilizing power of the acidic hypochlorous acid water is lost in a short period of time. Here, the quantum water has been recognized to have various effects, and the present inventor thought that the quantum water may contribute to the long-term continuation of the sterilizing power of the acidic hypochlorous acid water. When the present inventor diluted the acidic hypochlorous acid water with the quantum water, the present inventor surprisingly discovered that the sterilizing power of the acidic hypochlorous acid water was maintained over a long period of time. Therefore, the present inventor completed the present invention based on Examples shown below.

Figure 1:
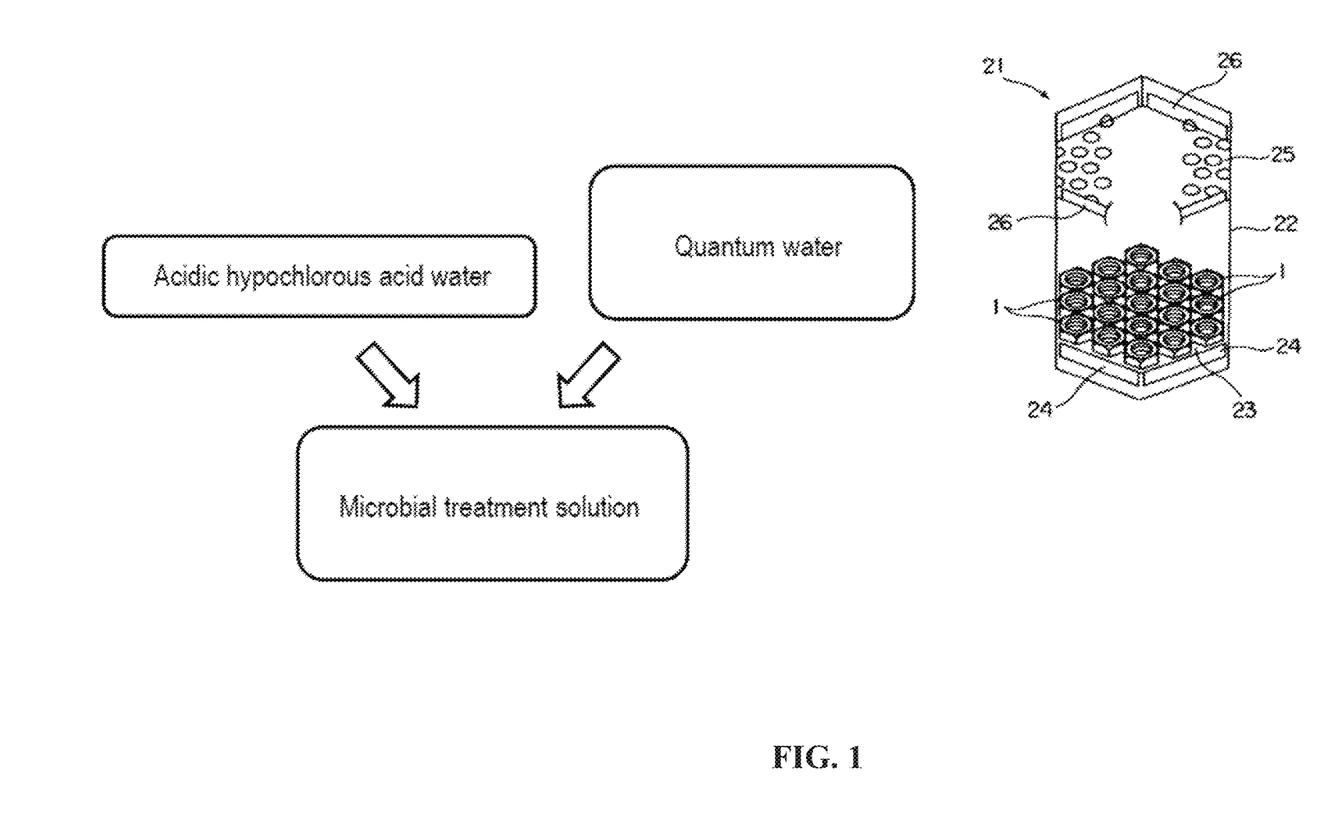
FIG. 1 is a conceptual view of a microbial treatment solution according to the present invention.

That is, as shown in FIG. 1, a microbial treatment solution according to the present invention includes an acidic hypochlorous acid water at a concentration of 0.5 wt % to 5.0 wt % for the total microbial treatment solution, and a quantum water is at a concentration of 90.0 wt % to 99.5 wt % for the total microbial treatment solution.

The quantum water is water passed through a quantum water converter, the quantum water converter is a liquid treatment apparatus 21 comprising a container 22 having an inlet and an outlet, and plural fragments 1 installed in the container 22. The fragment 1 is made of austenitic stainless steel or martensitic stainless steel, the fragment 1 has a regular hexagonal prism shape, the fragment 1 has a hole that penetrates a bottom surface and a top surface of the fragment 1, the hole is a circular cross section, and the fragment has a spiral groove going around an inner surface of the hole at least once, and the fragment 1 is heat-treated. The plural fragments 1 are arranged so that a central axis (the central axis of the fragment 1) of the fragments are parallel to each other, and the arrangement is maintained. The arranged plural fragments are positioned between the inlet and the outlet. The quantum water converter is described in detail in the PTL 1 of WO 03/05591, but this PTL 1 does not indicate that the quantum water is effective as a dilution water of the acidic hypochlorous acid water, as in the present invention.

The method for producing a microbial treatment solution according to the present invention includes a mixing step. The mixing step mixes an acidic hypochlorous acid water at a concentration of 0.5 wt % to 5.0 wt % for the total microbial treatment solution and a quantum water at a concentration of 90.0 wt % to 99.5 wt % for the total microbial treatment solution.

In this way, it is possible to maintain the sterilizing power of the acidic hypochlorous acid water for a long period of time. That is, the present invention utilizes the properties of the quantum water, the quantum water having various effects and being able to change into a state suitable for humans, animals and plants. It is possible to safely and effectively treat microorganisms such as viruses and bacteria over a long period of time by mixing the acidic hypochlorous acid water with the quantum water by taking advantage of the nature of the quantum water.

Since the microbial treatment solution according to the present invention has an antiviral effect and a deodorizing effect, it is possible to safely and securely use the microorganism with inactivating the microorganisms when the microbial treatment solution is used in a narrow space such as in a vehicle or in a building or in a care site.

Since the microbial treatment solution according to the present invention can maintain a residual chlorine concentration over a long period of time due to the quantum water, the microbial treatment solution can maintain the inactivation of microorganisms for a long period of time along with this.

By the way, there is no particular limitation on a type of the acidic hypochlorous acid water, for example, the acidic hypochlorous acid water may include either or a combination of strongly acidic hypochlorous acid water, weakly acidic hypochlorous acid water, slightly acidic hypochlorous acid water.

Here, since the strongly acidic hypochlorous acid water and the weakly acidic hypochlorous acid water are produced by electrolyzing an aqueous sodium chloride solution in an electrolytic cell with a septum, by using a highly safe sodium chloride aqueous solution, the strongly acidic hypochlorous acid water and the weakly acidic hypochlorous acid water do not contain hydrochloric acid. On the other hand, since the slightly acidic hypochlorous acid water is produced by electrolyzing hydrochloric acid or a mixture of hydrochloric acid and aqueous sodium chloride solution, by using hydrochloric acid, the slightly acidic hypochlorous acid water may contain hydrochloric acid. Thus, from a viewpoint of safety, the present invention preferably adopts either the strongly acidic hypochlorous acid water or the weakly acidic hypochlorous acid water, or a combination thereof.

There is no particular limitation on the residual chlorine concentration for the acidic hypochlorous acid water, for example, the residual chlorine concentration may be preferably in a range of 500 ppm to 3000 ppm, and may be more preferably in a range of 1000 ppm to 2000 ppm. Here, the acidic hypochlorous acid water corresponds to the undiluted solution.

Further, if the acidic hypochlorous acid water is acidic, there is no particular limitation on a pH of the acidic hypochlorous acid water, for example, the pH of the acidic hypochlorous acid water may be preferably in a range of 4.0 to 5.0.

Further, if the concentration of the acidic hypochlorous acid water is in the range of 0.5 wt % to 5.0 wt % for the total microbial treatment solution, there is no particular limitation on the concentration of the acidic hypochlorous acid water, for example, the concentration of the acidic hypochlorous acid water may be preferably in a range of 0.5 wt % to 2.0 wt % of the total microbial treatment solution, and may be more preferably in a range of 0.5 wt % to 1.0 wt % of the total microbial treatment solution.

If the quantum water is a water passed through the quantum water converter, there is no particular limitation on a type of the water, for example, the water may be a tap water, a distilled water, an ion-exchanged water, a purified water, or the like. The quantum water may be a water initially passed through the quantum water converter or may be a water repeatedly passed through the quantum water converter.

There is no particular limitation on a type of the quantum water converter, for example, the quantum water converter may include a commercial product name vG7 quantum water converter or the like. A size of the quantum water converter is typically in the range of 20 mm to 300 mm in diameter and a stroke of the quantum water converter is in the range of 50 mm to 400 mm. The quantum water converter may be one quantum water converter or plural quantum water converters connected together.

Explaining about the quantum water converter, as shown in FIG. 1, the quantum water converter comprises a container 22, a bottom plate 23, and a top plate 25, and those are made of a thin plate of stainless steel. The bottom plate 23 and the top plate 25 have a large number of through-holes with a diameter of 3 mm. The through-holes of the top plate 25 are shown partially omitted. The bottom plate 23 is folded at a peripheral portion 24 of the bottom plate 23, the bottom plate 23 is fixed to a bottom surface of the container 22 by partially welding this peripheral portion 24. A predetermined number (e.g. 19) of the fragments 1 are arranged on the bottom plate 23 in an OHA. Here, the OHA (Ortho-Hexagononal Arrangement) means a regular hexagonal array. The predetermined number of fragments 1 comprises one-stage, and these are stacked in a predetermined number of stages (e.g. nine stages). In addition, the second to ninth stages are omitted. When the first stage comprises 19 fragments 1, and the same stage exists up to the ninth stage, the total number of fragments 1 is 171. The OHA of each stage is stacked with a center of a concentric circle generally aligned up and down. As a result, the center axis of the fragment 1 arranged at a center point of each stage forms a substantially one virtual straight line. The top plate 25 is folded around a peripheral portion 26 of the top plate 25, the top plate 25 is fixed to a top surface of the container 22 by partially welding this peripheral portion 26. Regarding external dimensions of the container 22, a length of one side of the regular hexagonal prism shape is, for example, 15 mm, a height is 31 mm, and a distance between the top plate 25 and the bottom plate 23 is 22 mm. In the container 22, 19 fragments 1 of the first stage are stored in OHA. The same applies to the second to ninth stages. The fragments 1 are sandwiched between a side plate, the bottom plate 23, and the top plate 25 of the container, so that a movement of the fragments 1 is restricted, and the fragments 1 maintain the OHA arrangement.

Also, if the concentration of the quantum water is in the range of 90.0 wt % to 99.5 wt % for the total microbial treatment solution, there is no particular limitation on the concentration of the quantum water, for example, the concentration of the quantum water may be preferably in the range of 95.0 wt % to 99.5 wt % for the total microbial treatment solution, and may be more preferably in the range of 97.0 wt % to 99.5 wt % for the total microbial treatment solution. Also, there is no particular limitation on a pH of the quantum water, for example, the pH of the quantum water may be in the range of 6.5 to 7.5.

There is no particular limitation on a ratio of the concentration of the acidic hypochlorous acid water to the concentration of quantum water, for example, the ratio of the concentration of the acidic hypochlorous acid water to the concentration of quantum water may be preferably in the range of 1:10 to 1:150, and more preferably in the range of 1:30 to 1:100.

There is no particular limitation on a residual chlorine concentration for the microbial treatment solution, for example, the residual chlorine concentration for the microbial treatment solution may be preferably in the range of 5 ppm to 30 ppm, and more preferably in the range of 10 ppm to 20 ppm.

There is no particular limitation on a pH of the microbial treatment solution, for example, the pH of the microbial treatment solution may be preferably in the range of 5.0 to 7.0.

Other additive may be further mixed with the microbial treatment solution. The other additive may include organic acid selected from the group consisting of formic acid, acetic acid, propionic acid, sulfonic acid, sulfinic acid, thiocarboxylic acid, citric acid, malic acid, tartaric acid, oxalic acid, succinic acid, lactic acid, and combinations thereof. By including the organic acid, it contributes to maintaining the residual chlorine concentration for the microbial treatment solution, it is possible to preserve it for a long period of time while maintaining its sterilizing power. In addition, the organic acid may be more preferably succinic acid.

Also, the microbial treatment solution can be utilized in any manner. The microbial treatment solution may be directly sprayed or applied onto the object. The microbial treatment solution may be put into a humidifier and may be turned into a mist, and the mist may be used to sterilize the space. In addition, when the microbial treatment solution is turned into a mist, the residual chlorine concentration of the mist-like microbial treatment solution is 5 ppm or less, and there is no problem in safety at all.

The present invention is useful as a microbial treatment solution that is safe and highly effective in inactivating viruses, etc. and is applicable, for example, to all fields of hygiene, medical, care, transportation, service, retail, livestock industry, pet industry, and manufacturing industry. The present invention can be used safely and for an extended period of time, such as in fish farms, pig farms, and cattle farms in the livestock industry, pet farms in the pet industry, etc., cleaning of precision equipment in the manufacturing industry where alcohol cannot be used, or cleaning specially processed glass where alcohol cannot be used. The present invention can be utilized in various applications.

EXAMPLE

The present invention will be specifically described below by way of Examples and Comparative examples, and the present invention is not limited thereby.

Example 1

An acidic hypochlorous acid water and a quantum water were prepared. Here, the residual chlorine concentration of the acidic hypochlorous acid water was 1300 ppm and the pH of the acidic hypochlorous acid water was 4.0 to 5.0. The quantum water was also produced by passing a distilled water through a quantum water converter (Manufactured by Wellness Co., Ltd.) of a commercial product name vG7 (New G7). A microbial treatment solution produced by mixing the acidic hypochlorous acid water of 1 pt.wt. (part by weight) with the quantum water of 100 pts.wt. (parts by weight) was used as Example 1. The residual chlorine concentration for the microbial treatment solution of Example 1 was 13 ppm, and the pH of the microbial treatment solution of Example 1 was 6.5. In this case, the concentration of the acidic hypochlorous acid water for the total microbial treatment solution is $1/(1+100)=0.99$ wt %, and the concentration of the quantum water for the total microbial treatment solution is $100/(1+100)=99.01$ wt %.

Reference Example 1

Distilled water alone was used as Reference Example 1.

Comparative Example 1

The microbial treatment solution produced in the same manner as in Example 1 except that the quantum water was changed to distilled water was used as Comparative Example 1

Comparative Example 2

The quantum water alone used in Example 1 was used as Comparative Example 2.
Evaluation Method of Microbial Treatment Solution
(1) An Inactivation Test for *E. coli*

After 3 ml of each of the microbial treatment solutions of Example 1, Reference Example 1, and Comparative Example 1-2 was put in a test tube, 10 mL of a *E. coli* solution with a viable bacteria count of $6.3 \times 10^7$ CFU/100 ml was added to the test tube with a digital pipette, the microbial treatment solution was reacted with the *E. coli* solution, and a reaction solution in the test tube was left. Then, the reaction solution after a predetermined leaving time has passed from a point of immediately addition was taken, and the viable bacteria count (CFU/100 ml) of *E. coli* was measured using the taken reaction solution. The predetermined leaving time was set for 1 minute, 5 minutes, 60 minutes (1 hour), 1,440 minutes (24 hours), 43,200 minutes (one month=30 days) and it was confirmed whether the microbial treatment solution maintains its sterilizing power for a long period of time.
(2) Test of Residual Chlorine Concentration.

After 3 ml of each of the microbial treatment solutions of Example 1, Reference Example 1, and Comparative Example 1-2 was put in a test tube, 10 mL of a commercial residual chlorine detection reagent (DPD solution, N, N-diethylparaphenylenediamine solution) was added to the test tube with a digital pipette, the microbial treatment solution was reacted with the commercial residual chlorine detection reagent, and a reaction solution in the test tube was left. After 43,200 minutes (1 month=30 days) had passed from a point of immediately addition, a condition of a dyeing was confirmed. For test tubes with good coloring, an absorbance at 540 nm was measured, and the residual chlorine concentration was measured using a calibration curve.
Evaluation Results of the Microbial Treatment Solutions
(1) The Inactivation Test for *E. coli*

Figure 2:
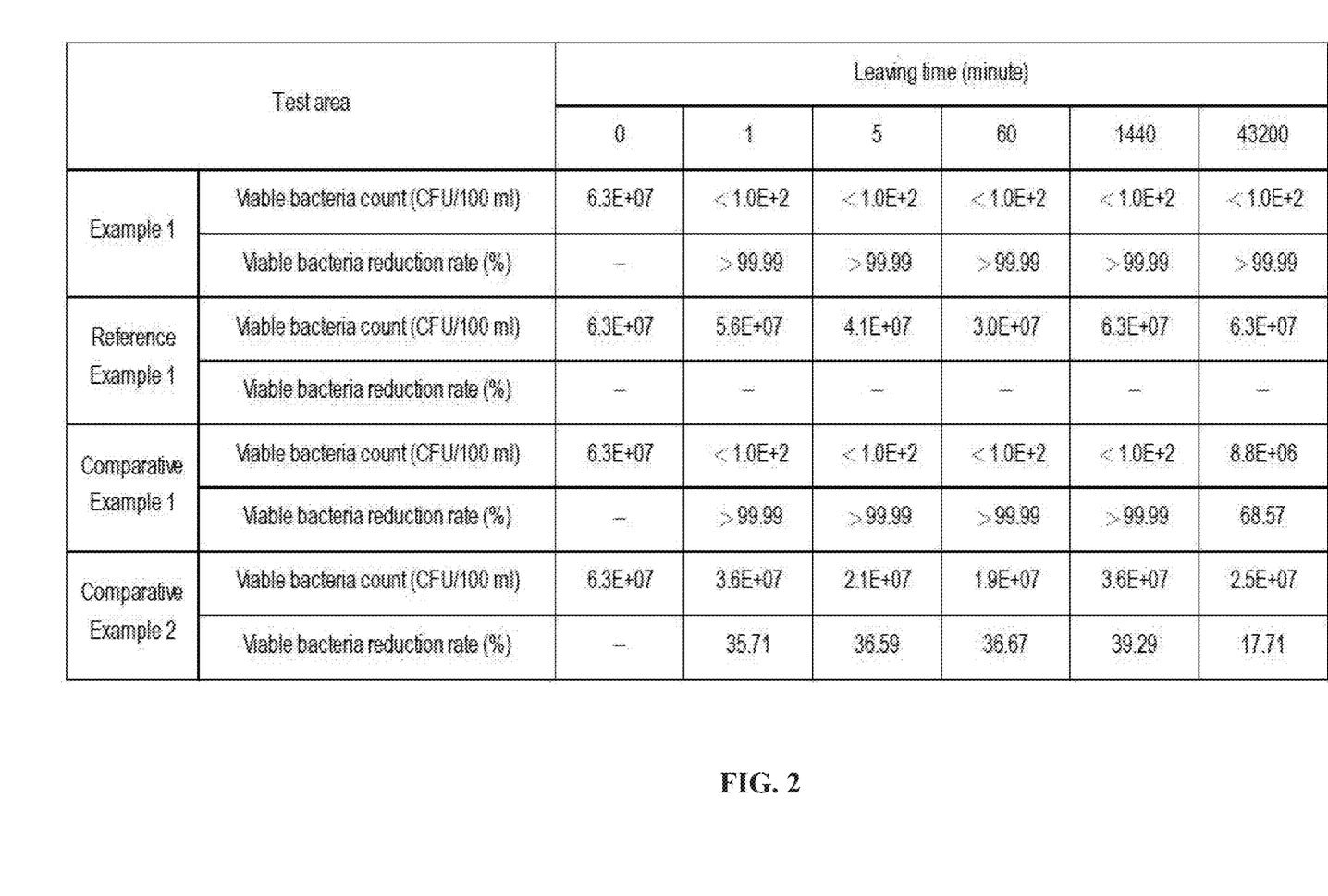
FIG. 2 is a table of results of inactivation test of *E. coli* in Example 1, Reference Example 1, Comparative Examples 1-2.
Figure 3:
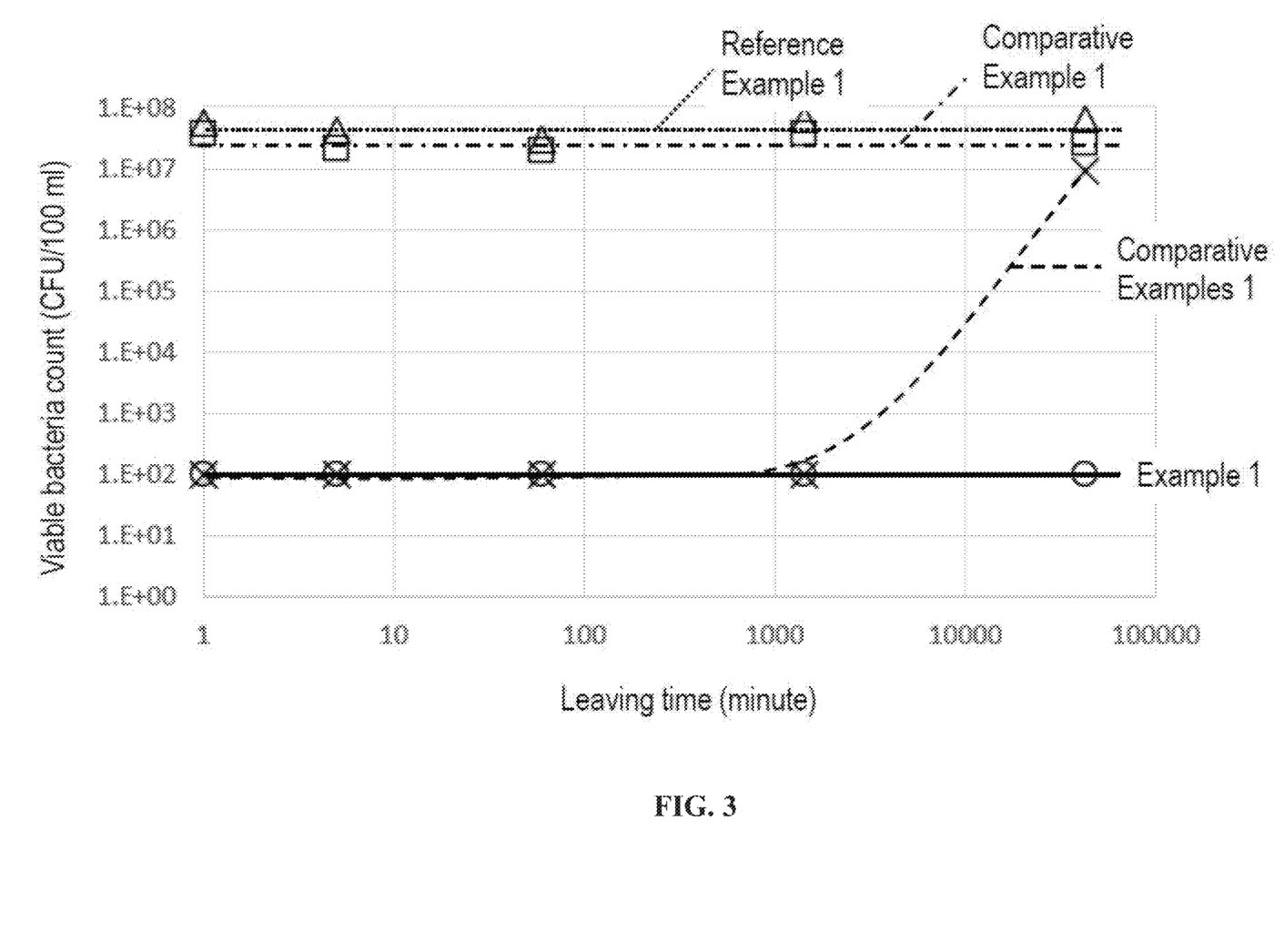
FIG. 3 is a graph of results of inactivation test of *E. coli* in Example 1, Reference Example 1, Comparative Examples 1-2.

FIG. 2 shows a table of the results of the inactivation test of *E. coli* in Example 1, Reference Example 1, Comparative Examples 1-2. FIG. 3 shows a graph of the results of the inactivation test of *E. coli* in Example 1, Reference Example 1, Comparative Examples 1-2. As shown in FIGS. 2-3, Reference Example 1 and Comparative Example 2 could not inactivate *E. coli*. It was found that Comparative Example 1 could inactivate *E. coli*, but when the leaving time was 43200 minutes, the viable bacteria count of $8.8 \times 10^6$ CFU/100 ml was measured in Comparative Example 1, so Comparative Example 1 could not inactivate *E. coli* at 43200 minutes of the leaving time. On the other hand, even if the leaving time was 43200 minutes in Example 1, the viable bacteria count of less than $1.0 \times 10$ CFU/100 ml was measured in Example 1, Example 1 could continuously inactivate *E. coli*. In other words, it was found that the sterilizing power of the acidic hypochlorous acid water in Example 1 was maintained even after one month had passed.

Figure 4:
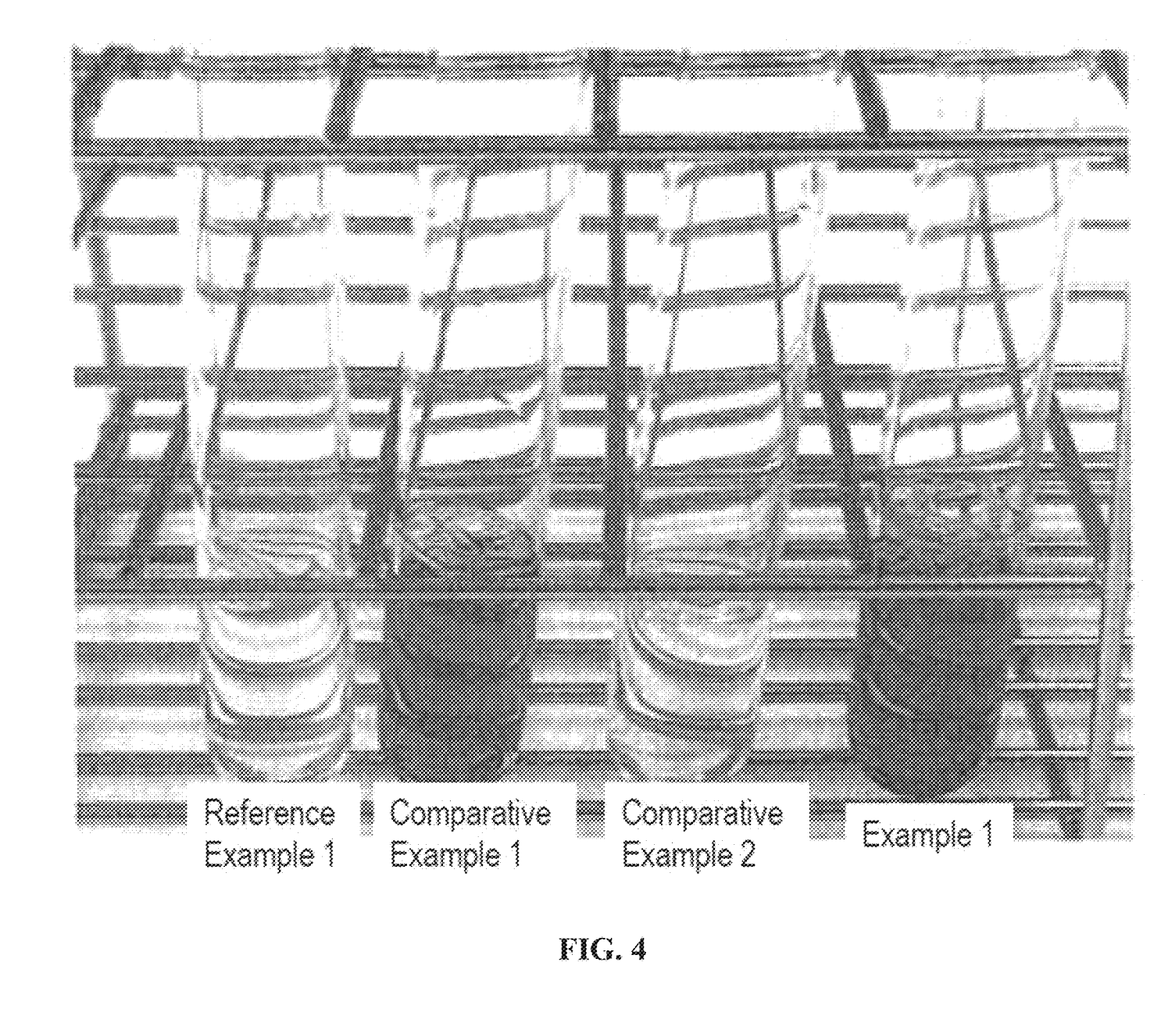
FIG. 4 is a photograph of a test tube after one month in Example 1, Reference Example 1, Comparative Examples 1-2.

(2) Test of Residual Chlorine Concentration
FIG. 4 is a photograph of the test tube after one month in Example 1, Reference Example 1, Comparative Examples 1-2. As shown in FIG. 4, it was found that there is no residual chlorine concentration in Reference Example 1 and Comparative Example 2, so Reference Example 1 and Comparative Example 2 remained transparent. And it was found that Comparative Example 1 slightly colored. On the other hand, it was found that Example 1 strongly colored compared to Comparative Example 1 and the residual chlorine concentration is high in Example 1. Here, when the residual chlorine concentration in Example 1 was measured, the residual chlorine concentration was 13 ppm, and the residual chlorine concentration was the same as the initial level. It was found that the residual chlorine concentration is maintained for a long period of time.

Example 2

The microbial treatment solution produced in the same manner as in Example 1 except that 1 pt.wt. of succinic acid was further added was used as Example 2. The residual chlorine concentration of the microbial treatment solution of Example 2 was 13 ppm, and the pH of the microbial treatment solution of Example 2 was 6.5. In this case, the concentration of the acidic hypochlorous acid water for the total microbial treatment solution is $1/(1+100+1)=0.98$ wt %, the concentration of the quantum water for the total microbial treatment solution is $100/(1+100+1)=98.04$ wt %, and the concentration of the succinic acid is $1/(1+100+1)=0.98$ wt %.

Regarding Example 2, when an inactivation test for *E. coli* and a test for residual chlorine concentration were similarly conducted, even if the leaving time was 43200 minutes in Example 2, the viable bacteria count of less than $1.0 \times 10$ CFU/100 ml was measured in Example 2, it was found that Example 2 could continuously inactivate *E. coli*. When the residual chlorine concentration in Example 2 was measured, the residual chlorine concentration was 13 ppm, and the residual chlorine concentration was the same as the initial level, and it was found that the residual chlorine concentration is maintained for a long period of time.

Example 3

The microbial treatment solution produced in the same manner as in Example 1 except that 1 pt.wt of the acidic hypochlorous acid water was mixed with 50 pt.wt. of the quantum water was used as Example 3. The residual chlorine concentration of the microbial treatment solution of Example 3 was 26 ppm, and the pH of the microbial treatment solution of Example 3 was 6.0. In this case, the concentration of the acidic hypochlorous acid water for the total microbial treatment solution is $1/(1+50)=1.96$ wt %, and the concentration of the quantum water for the total microbial treatment solution is $50/(1+50)=98.04$ wt %.

Example 4

The microbial treatment solution produced in the same manner as in Example 1 except that 1 pt.wt of the acidic hypochlorous acid water was mixed with 30 pt.wt. of the quantum water was used as Example 4. The residual chlorine concentration of the microbial treatment solution of Example 4 was 43 ppm, and the pH of the microbial treatment solution of Example 4 was 5.8. In this case, the concentration of the acidic hypochlorous acid water for the total microbial treatment solution is 1/(1+30)=3.22 wt %, and the concentration of the quantum water for the total microbial treatment solution is 30/(1+30)=96.78 wt %.

Regarding Examples 3 and 4, when an inactivation test for *E. coli* and a test for residual chlorine concentration were similarly conducted, even if the leaving time was 43200 minutes in Examples 3 and 4, the viable bacteria count of less than 1.0×10 CFU/100 ml was measured in Examples 3 and 4, it was found that Examples 3 and 4 could continuously inactivate *E. coli*. When the residual chlorine concentration in Examples 3 and 4 was measured, the residual chlorine concentration was 13 ppm, and the residual chlorine concentration was the same as the initial level, and it was found that the residual chlorine concentration is maintained for a long period of time.

Example 5

The microbial treatment solution produced in the same manner as in Example 1 except that 1 pt.wt of the acidic hypochlorous acid water was mixed with 199 pt. wt. of the quantum water was used as Example 5. The residual chlorine concentration of the microbial treatment solution of Example 5 was 10 ppm, and the pH of the microbial treatment solution of Example 5 was 6.7. In this case, the concentration of the acidic hypochlorous acid water for the total microbial treatment solution is 1/(1+199)=0.50 wt %, and the concentration of the quantum water for the total microbial treatment solution is 199/(1+199)=99.50 wt %.

Example 6

The microbial treatment solution produced in the same manner as in Example 1 except that 1 pt.wt of the acidic hypochlorous acid water was mixed with 19 pt.wt. of the quantum water was used as Example 6. The residual chlorine concentration of the microbial treatment solution of Example 6 was 50 ppm, and the pH of the microbial treatment solution of Example 6 was 5.5. In this case, the concentration of the acidic hypochlorous acid water for the total microbial treatment solution is 1/(1+19)=5.00 wt %, and the concentration of the quantum water for the total microbial treatment solution is 19/(1+19)=95.00 wt %.

Example 7

The microbial treatment solution produced in the same manner as in Example 1 except that 1 pt.wt of the acidic hypochlorous acid water and 1 pt.wt of perfume were mixed with 18 pt.wt. of the quantum water was used as Example 7. The residual chlorine concentration of the microbial treatment solution of Example 7 was 50 ppm, and the pH of the microbial treatment solution of Example 7 was 5.4. In this case, the concentration of the acidic hypochlorous acid water for the total microbial treatment solution is 1/(1+18+1)=5.00 wt %, the concentration of the quantum water for the total microbial treatment solution is 18/(1+18+1)=90.00 wt %, and the concentration of the perfume for the total microbial treatment solution is 1/(1+18+1)=5.00 wt %.

Regarding Examples 5-7, when an inactivation test for *E. coli* and a test for residual chlorine concentration were similarly conducted, even if the leaving time was 43200 minutes in Examples 5-7, the viable bacteria count of less than 1.0×10 CFU/100 ml was measured in Examples 5-7, it was found that Examples 5-7 could continuously inactivate *E. coli*. When the residual chlorine concentration in Examples 5-7 was measured, the residual chlorine concentration was 13 ppm, and the residual chlorine concentration was the same as the initial level, and it was found that the residual chlorine concentration is maintained for a long period of time.

INDUSTRIAL APPLICABILITY

As described above, the microbial treatment solution and the method of producing the microbial treatment solution according to the present invention is applicable to all fields of hygiene, medical, care, transportation, service, retail, livestock industry, pet industry, and manufacturing industry. It is effective as the microbial treatment solution and the method of producing the microbial treatment solution that can maintain the sterilizing power of acidic hypochlorous acid water for a long period of time.

What is claimed is:

1. A method of a microbial treatment solution comprising:
   a mixing step mixes an acidic hypochlorous acid water at a concentration of 0.5 wt % to 5.0 wt % for the total microbial treatment solution, and a quantum water at a concentration of 95.5 wt % to 99.5 wt % for the total microbial treatment solution;
   wherein:
   the quantum water is water passed through a quantum water converter;
   the quantum water converter comprising a container having a liquid inlet and an outlet and plural fragments installed in the container, the fragment is made of austenitic stainless steel or martensitic stainless steel, the fragment has a regular hexagonal prism shape, the fragment has a hole that penetrates a bottom surface and a surface of the fragment, the hole is a circular cross section, the fragment has a spiral groove on an inner surface of the hole that goes around the inner surface once or more, the fragment heat treated, the plural fragments are arranged between the inlet and the outlet so that they are parallel to six side surfaces of the regular hexagonal prism, and a central axis perpendicular to both end faces of the regular hexagonal prism are parallel to each other;
   a pH of the quantum water is in the range of 6.5 to 7.5;
   the acidic hypochlorous acid water does not contain hydrochloric acid produced by electrolyzing an aqueous sodium chloride solution in an electrolytic cell with a septum;
   a residual chlorine concentration of the acidic hypochlorous acid water is in the range of 500 ppm to 3000 ppm;
   a pH of the acidic hypochlorous acid water is in the range of 4.0 to 5.0;
   the microbial treatment solution is obtained by diluting the acidic hypochlorous acid water with the quantum water;
   a total concentration of the acidic hypochlorous acid water and the quantum water is 100.0 wt %;
   a residual chlorine concentration of the microbial treatment solution is in the range of 5 ppm to 30 ppm;
   a pH of the microbial treatment solution is in the range of 5.0 to 7.0; and
   even if a leaving time is 43200 minutes in the microbial treatment solution, a viable bacteria count for *E coli* in the microbial treatment solution is measured to be less than 1.0×10 CFU/100 ml.

2. The method according to claim 1, wherein the microbial treatment solution further includes succinic acid.

3. The method according to claim 1, wherein a ratio of the concentration of the acidic hypochlorous acid water to the concentration of quantum water is in the range of 1:30 to 1:100.

4. The method according to claim 1, wherein the microbial treatment solution further includes organic acid selected from the group consisting of formic acid, acetic acid, propionic acid, sulfonic acid, sulfinic acid, thiocarboxylic acid, citric acid, malic acid, tartaric acid, oxalic acid, succinic acid, lactic acid, and combinations thereof.

5. The method according to claim 1, wherein the acidic hypochlorous acid water is a strongly acidic hypochlorous acid water or a weakly acidic hypochlorous acid water.

6. The method according to claim 1, wherein the residual chlorine concentration of the microbial treatment solution is in the range of 10 ppm to 20 ppm.

7. The method according to claim 1, wherein the microbial treatment solution further includes perfume.

8. The method according to claim 1, wherein:
the acidic hypochlorous acid water is a strongly acidic hypochlorous acid water or a weakly acidic hypochlorous acid water; and
the residual chlorine concentration of the microbial treatment solution is in the range of 10 ppm to 20 ppm.

9. The method according to claim 1, wherein:
the acidic hypochlorous acid water is a strongly acidic hypochlorous acid water or a weakly acidic hypochlorous acid water; and
the residual chlorine concentration of the microbial treatment solution is in the range of 10 ppm to 20 ppm; and
the microbial treatment solution includes succinic acid.

10. The method according to claim 1, wherein:
the acidic hypochlorous acid water is a strongly acidic hypochlorous acid water or a weakly acidic hypochlorous acid water;
the residual chlorine concentration of the microbial treatment solution is in the range of 10 ppm to 20 ppm; and
the microbial treatment solution includes organic acid selected from the group consisting of formic acid, acetic acid, propionic acid, sulfonic acid, sulfinic acid, thiocarboxylic acid, citric acid, malic acid, tartaric acid, oxalic acid, succinic acid, lactic acid, and combinations thereof.

* * * * *